[19] United States Patent
Clark et al.

[11] Patent Number: 4,788,292
[45] Date of Patent: Nov. 29, 1988

[54] PERFLUOROALKYL SUBSTITUTED BENZOTRIAZOLES

[75] Inventors: Kirtland P. Clark, Bethel, Conn.; Athanasios Karydas, Brooklyn, N.Y.

[73] Assignee: Ciba-Geigy Corporation, Ardsley, N.Y.

[21] Appl. No.: 892,219

[22] Filed: Jul. 31, 1986

[51] Int. Cl.[4] .................. C07D 249/18; C23F 11/14
[52] U.S. Cl. .................................. 548/260; 544/342; 546/107; 548/127; 548/151; 548/257; 548/259; 548/261; 549/551; 549/552; 549/556; 549/558; 549/563
[58] Field of Search .................... 252/50, 51, 51.15 R, 252/390, 391, 392; 548/261, 257, 259, 260

[56] References Cited

U.S. PATENT DOCUMENTS

| | | | |
|---|---|---|---|
| 3,658,720 | 4/1972 | McDougall et al. | 252/392 |
| 3,849,433 | 11/1974 | Butula | 548/257 |
| 4,028,268 | 6/1977 | Sullivan, 3rd et al. | 252/392 |
| 4,212,754 | 7/1980 | Chibnik | 548/260 |
| 4,519,928 | 5/1985 | Braid | 548/257 |
| 4,636,359 | 1/1987 | Penninger | 422/13 |
| 4,642,221 | 2/1987 | Hansen et al. | 422/16 |
| 4,647,392 | 3/1987 | Darden et al. | 252/75 |
| 4,683,071 | 6/1987 | Regenass | 548/260 |

FOREIGN PATENT DOCUMENTS

| | | | |
|---|---|---|---|
| 2026493 | 9/1970 | France | 548/257 |
| 47-11074 | 4/1972 | Japan | 548/259 |
| 47-43949 | 7/1972 | Japan | 548/259 |

OTHER PUBLICATIONS

H. Leidheiser, Jr. (1978) Corrosion Control by Coatings. Science Press, Princeton, NJ pp. 279-317.

Primary Examiner—Donald G. Daus
Assistant Examiner—Mark W. Noel
Attorney, Agent, or Firm—Luther A. R. Hall; Irving M. Fishman

[57] ABSTRACT

Compounds of the formula

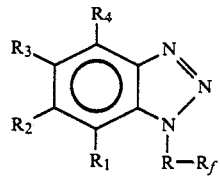

I or

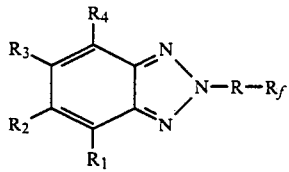

II wherein $R_1$, $R_2$, $R_3$ and $R_4$, independently of one another, represent hydrogen, hydroxy or halogen or are alkyl, alkoxy, alkanoyloxy, or alkanoylamino groups which are unsubstituted or substituted by alkoxy, hydroxyl, halogen, aryl, cycloalkyl, azacycloalkyl, cyano or by polyalkyleneoxy, or two or more of adjacent $R_1$-$R_4$ together form one or more fused rings of 5-8 members each; R is alkylene of up to 16 carbon atoms which is unsubstituted or substituted by hydroxy, lower alkoxy, or halo and which may be interrupted by oxygen, sulfur, carboxamido, sulfonamido, aminosulfonyl, aminocarbonyl, carbonyloxy, sulfinyl, or sulfonyl; and $R_f$ is perfluoroalkyl or perfluoroalkoxyalkyl of 4 to 16 carbon atoms; or mixtures thereof. Such compounds are useful as oil soluble corrosion inhibitors.

12 Claims, No Drawings

PERFLUOROALKYL SUBSTITUTED BENZOTRIAZOLES

DETAILED DESCRIPTION OF THE INVENTION

The present invention relates to perfluoroalkyl containing triazoles which are useful as oil soluble corrosion inhibitors for metal surfaces.

More specifically, one embodiment of the present invention relates to a compound of the formula

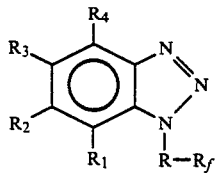

or

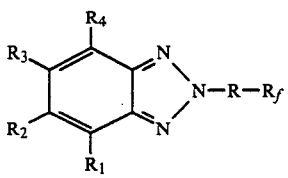

wherein R is alkylene of up to 12 carbon atoms which is unsubstituted or substituted by hydroxy, lower alkoxy or halo and which may be interrupted independently by one or two oxygen, sulfur, carboxamido, sulfonamido, aminocarbonyl, aminosulfonyl, carbonyloxy, sulfinyl or sulfonyl; $R_f$ is perfluoroalkyl or perfluoroalkoxyalkyl of 4 to 16 carbon atoms; and $R_1$–$R_4$ are each independently hydrogen, hydroxy or halogen, or are alkyl of up to 10 carbon atoms, lower alkanoyloxy, lower alkoxy, or lower alkanoylamino, each of which are unsubstituted or substituted by $C_6$–$C_{10}$-aryl, $C_4$–$C_7$-cycloalkyl, $C_3$–$C_6$-azacycloalkyl, lower alkoxy, hydroxy, halogen, cyano, or by poly lower alkyleneoxy, or two or more of $R_1$–$R_4$ together form fused rings having 5–8 ring atoms each; or mixtures thereof.

Preferably, $R_1$, $R_2$, $R_3$ and $R_4$ are hydrogen, lower alkyl or lower alkoxy being unsubstituted or substituted as above, preferably unsubstituted. Most preferably $R_1$–$R_4$ are hydrogen.

R is preferably alkylene of 2 to 10 carbon atoms which is unsubstituted or substituted by hydroxy and is interrupted independently by one or two oxygen atoms, a sulfur atoms, a carboxamido group or a sulfonamido group. Most preferably, R is alkylene of 6 to 10 carbon atoms substituted by hydroxy and is interrupted independently by oxygen or sulfur.

$R_f$ is preferably perfluoroalkyl of 4 to 16 carbon atoms, most preferably of 6 to 12 carbon atoms.

As used throughout this specification, "lower" designates up to 7, preferably up to 4, carbon atoms.

By poly lower alkyleneoxy is meant preferably poly $C_2$–$C_3$alkyleneoxy, terminated by hydroxy or $C_2$–$C_3$alkylene and having from 3 to about 40 alkylenoxy units.

Aryl is preferably phenyl or naphthyl.

Cycloalkyl is preferably cyclopentyl or cyclohexyl.

Azacycloalkyl is preferably pyrrolidinyl such as the 2-, or 3- pyrrolidinyl, or piperidinyl, such as the 2-, 3-, or 4- piperidinyl wherein the nitrogen thereof is unsubstituted or substituted by lower alkyl, especially methyl or ethyl.

Where two of adjacent $R_1$, $R_2$, $R_3$ or $R_4$ together form fused rings having 5 to 8 ring atoms, the ring atoms typically consist of carbon and/or nitrogen. Suitable fused rings, taken together with the respective carbon atoms to which $R_1$, $R_2$, $R_3$ and $R_4$ are attached include, for example, the fused benzene, quinoline, benzopyrazine, thiadiazole, thiazole, naphthalene, or bicyclopentadiene.

Also, three adjacent moieties of $R_1$, $R_2$, $R_3$ or $R_4$ can, together with the benzene ring to which they are attached, form a fused ring system, such as acenaphthylene.

Further, two non-adjacent, $R_1$, $R_2$, $R_3$ or $R_4$ can, taken together, form a fused ring system, representing methylene, ethylene or oxa.

Highly preferred are those compounds wherein $R_1$, $R_2$, $R_3$ and $R_4$ independently represent hydrogen, lower alkyl, or lower alkoxy. Most preferred are those compounds wherein $R_1$, $R_2$, $R_3$ and $R_4$ are hydrogen.

Compounds of the most preferred embodiment can be obtained by reacting triazoles of the formula

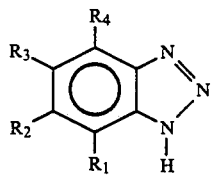

with epoxides of the formula

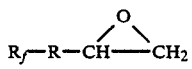

The reaction is optionally carried out in the presence of a suitable diluent or solvent such as benzene, methylene chloride, chloroform, acetone, diethyl ether, toluene and the like. $R_f$, R, $R_1$, $R_2$, $R_3$, and $R_4$ are as previously defined. If desired, the reaction can be optionally conducted in the presence of a Lewis acid, such as $AlCl_3$ or $BF_3$, at a temperature between about 0° C. to about 120° C.

Typical known epoxides which are included within the context of this invention are:

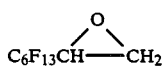

$C_6F_{13}CH=CHCH_2-\overset{O}{\overset{|}{CH}-CH_2}$ $C_8F_{17}SO_2\overset{CH_3}{\overset{|}{N}}CH_2\overset{O}{\overset{|}{CH}-CH_2}$ $C_{12}F_{25}CH_2CH_2SCH(CH_3)CH_2OCH_2\overset{O}{\overset{|}{CH}-CH_2}$ $C_6F_{13}CH_2CH_2N(CH_3)CH_2CH_2CH_2S(CH_2)_3OCH_2\overset{O}{\overset{|}{CH}-CH_2}$ $C_8F_{17}CH_2CH_2SCH_2CH_2CH_2SCH(CH_3)CH_2OCH_2\overset{O}{\overset{|}{CH}-CH_2}$ $C_8F_{17}SO_2N(C_2H_5)CH_2CH_2S(CH_2)_3OCH_2\overset{O}{\overset{|}{CH}-CH_2}$ $C_8F_{17}CH_2CH_2SO_2NHCH_2CH_2CH_2SCH_2CH(CH_3)CH_2OCH_2\overset{O}{\overset{|}{CH}-CH_2}$ -continued $(CF_3)_2CFOCF_2CF_2CH_2CH_2SCH_2CH_2CH_2OCH_2\overset{O}{\overset{|}{CH}-CH_2}$ $CF_3CF_2CH_2SO_2CH_2CH_2CH_2OCH_2\overset{O}{\overset{|}{CH}-CH_2}$ $C_8F_{17}CH_2CH_2OCH_2CH_2CHSCH_2CH(CH_3)CH_2OCH_2\overset{O}{\overset{|}{CH}-CH_2}$ Typical known triazoles included within the context of the invention include:

-continued

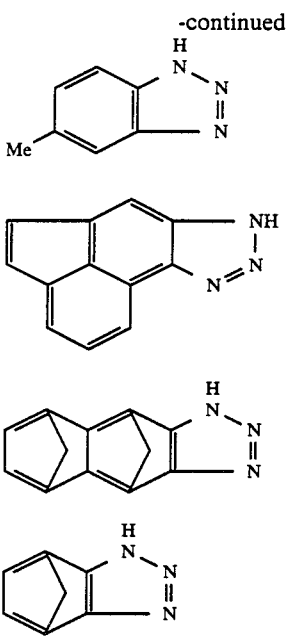

Alternatively, the compounds of the instant invention may be prepared by reacting a triazole of formula III with a compound of the formula

IV where X is a leaving group, and Rf and R are as defined as above.

Suitable leaving groups, X, include for example halo, especially chloro, bromo and iodo, and the like. The reaction is generally conducted at a temperature between about 0° C. and 120° C., with removal of the by-product HX, for example by passing an inert gas through the reaction mixture, such as air or nitrogen, or by conducting the reaction in the presence of a base, such as an alkali, or alkaline earth metal, hydroxide, carbonate or bicarbonate, or in the presence of ammonia, ammonium hydroxide or an amine, such as triethyl amine.

Suitable compounds of the formula IV include, for example $C_6F_{13}CH_2CH_2I$
$C_8F_{17}CH_2CH_2I$
$C_6F_{13}CH_2CH_2Br$
$C_6F_{13}CH_2CH_2Cl$
$C_8F_{17}CH_2CH_2Br$
$C_8F_{17}CH_2CH_2OCH_2CH_2Br$
$C_8F_{17}CH_2CH_2SO_2NHCH_2CH_2Br$
$C_8C_{17}CH_2CH_2CONHCH_2CH_2Br$
$C_8F_{17}CH_2CH_2SO_2CH_2CH_2Br$ The compounds of the invention are particularly useful as oil soluble corrosion inhibitors for metals against corrosion from corrosive acids, brines, oxidation and the like. They are suitably employed in compositions having an oil component which will come into contact with at least one of the metals below. Preferably, the oil is selected from lubricating oils, hydrocarbon diluents, such as toluene, xylene, fuel oil, acetone and the like. The preferred concentration of the compounds of formulae I and/or II in the composition is about 0.01% to about 5%, preferably about 0.01 to about 0.1% by weight.

Metals for which corrosion is inhibited by the invention include iron, steel, copper, brass and preferably are steel or iron.

Their effectiveness of the compounds of the invention as corrosion inhibitors was determined by the following procedure:

Corrosion test coupons [SAE 1010, mild steel, cold-rolled, polished (#280 grit)] were immersed at room temperature in a 0.4% (w/w) toluene solution of the inhibitor sample for 30 minutes. The coupons were then taken out of the solution slowly and dried in ambient air for 30 minutes before weighing. Each weighed coupon was completely immersed in the test solution (5% HCl solution, 110 ml total volume) contained in a 4 oz. glass jar and held at room temperature for 4 hours. The weight loss after the 4 hour period was measured. Triplicate runs were made for each inhibitor sample.

For a clearer understanding of the invention, the following specific examples are given. These examples are intended to be merely illustrative of the invention and not a limitation thereof. Unless otherwise specified all parts are by weight.

EXAMPLE 1

A mixture of 3.01 g benzotriazole (0.0252 mole) and 52.04 g toluene is heated at 80° C. until a clear liquid is obtained. Then 10.0 g

(0.0229 mole) are added and the reaction mixture is heated at 80° for 3 hours. Then 0.04 g boron trifluoride etherate are added and the reaction mixture is heated at 80° for another 26 hours. Removal of the toluene affords a product containing a mix of two isomers with the following structures I and II, as determined by NMR:

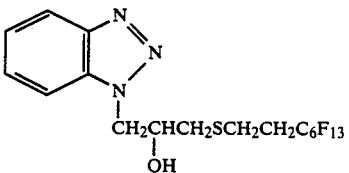

and

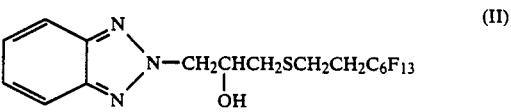

Analysis: Calculated (percent): C, 37.3; H, 2.6; N, 8.2; F, 43.5; Found (percent: C, 37.3; H, 2.6; N, 8.3; F, 42.8.

EXAMPLE 2

A mixture of 4.37 tolutriazole (0.0326 mole) and 77.48 g toluene is heated at 80° C. until a clear liquid is obtained. Then 15.0 g

(0.0296 mole) are added and the reaction mixture is heated at 80° for 3 hours. Then 0.04 g boron trifluoride etherate are added and the reaction mixture is heated at 80° for another 26 hours. Removal of the toluene affords a product containing a mix of isomers with the following structures are determined by NMR:

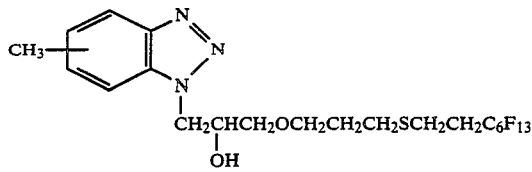

and

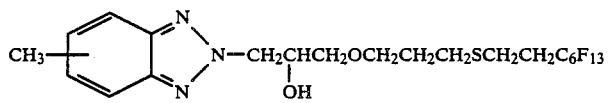

Analysis: Calculated (percent): C, 39.8; H, 3.5; N, 7.1; F, 38.6; Found (percent): C, 41.2; H, 3.6; N, 7.5; F, 37.3.

EXAMPLE 3

A mixture of 1.57 benzotriazole (0.0132 mole) and 24.28 g toluene is heated at 80° C. until a clear liquid is obtained. Then, 4.5 g of 1, 1H, 2H, 3, 3H perfluoro nonylene oxide are added and the reaction mixture is heated at 80° for 2 hours. Then 0.04 g boron trifluoride etherate are added and the reaction mixture is heated at 80° for another 25 hours. A solid precipitates. It is collected by filtration and washed with hexane. A pale beige product is obtained with the following structure as determined by NMR:

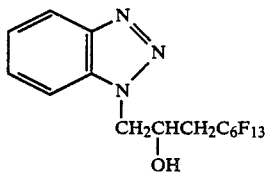

Analysis: Calculated (percent): C, 36.9; H, 2.0; N, 9.1; F, 48.7; Found (percent): C, 36.7; H, 2.0; N, 8.9; F, 49.1.

EXAMPLE 4

Compounds from the previous examples are screened as corrosion inhibitors by the method previously described.

| Compound from Example | Weight Loss (mg) | % Protection[a] |
| --- | --- | --- |
| 1 | 2.8 ± 0.6 | 93 |
| 2 | 3.4 ± .1 | 91 |
| 3 | 24 ± 5 | 38 |
| Benzotriazole | 36 ± 7 | None |
| Control | 38 ± 5 | — |

[a]% protection = $(\Delta W_c - \Delta W_s) \cdot 100 / \Delta W_c$ where $\Delta W_c$ = weight loss of the control coupon, $\Delta W_s$ = weight loss of the coated coupon.

EXAMPLE 5

A mixture of 0.66 benzotriazole (0.0054 mole) and 13.40 g chloroform is heated at 60° C. until a clear liquid is obtained. Then 2.69 g of

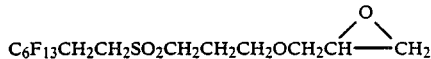

are added and the reaction mixture is heated at 60° for 2 hours 40 minutes. Removal of the chloroform affords a product with the following structures, I and II, as determined by NMR:

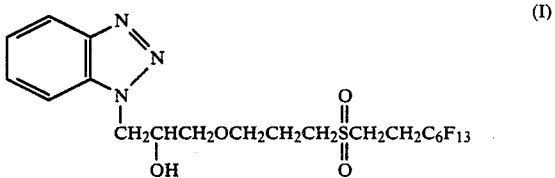

and

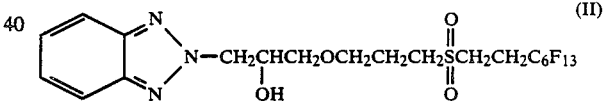

EXAMPLE 6

A mixture of 2.10 g benzotriazole (0.0176 mole), 2.44 g potassium carbonate (0.0176 mole), and 21.60 g acetone is heated under reflux. A solution of 9.22 g RfCH$_2$CH$_2$I (Rf=C$_{2n}$F$_{4n+1}$ where n=2 through 8) (0.0160 mole) and 33.40 g acetone is added, and the reaction mixture is heated under reflux for 20 hours. A clear liquid is obtained upon filtration. Removal of the acetone affords a solid, which is then added to 0.40 hexafluoroxylene. The mixture is heated on a steam bath for 30 minutes, filtered to remove insolubles, and then placed under high vacuum (0.05 mmHg, 65Z). The product is a pale brown waxy solid with the following structures, I and II, as determined by NMR:

and

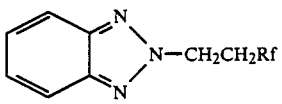 (II)

EXAMPLE 7

Compounds from the previous examples were screened as corrosion inhibitors according to the method previously described.

| Compound from Example | Weight Loss (mg) | % Protection |
|---|---|---|
| Control | 34 ± 3 | — |
| 5 | 27 ± 10 | 20 |
| 6 | 24 ± 6 | 28 |

EXAMPLE 8

A mixture of 1.58 benzotriazole (0.0131 mole) and 7.0 g

(0.0114 mole) and 34.24 g toluene, is heated to reflux (110°–111° C.) for 10.25 hours. Then 0.02 g boron trifluoride etherate are added and the reaction mixture is heated under reflux for 45 minutes. Removal of the toluene affords a product containing a mix of two isomers with the following structures I and II, as determined by NMR:

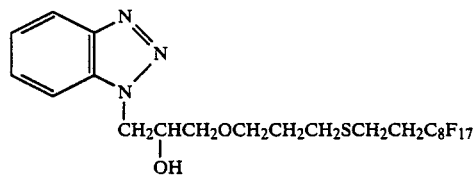 (I)

and

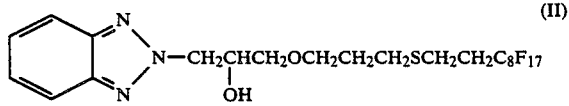 (II)

Analysis: Calculated (percent): C, 37.0; H, 2.8; N, 6.7; F, 45.3; Found (percent): C, 37.3; H, 2.8; N, 6.7; F, 43.6.

EXAMPLE 9

Compounds from the previous examples were screened as corrosion inhibitors according to the method previously described.

| Compound from Example | Weight Loss (mg) | % Protection |
|---|---|---|
| Control | 41 ± 4 | — |
| 8 | 14 ± 1 | 66 |

What is claimed is:

1. A compound of the formula

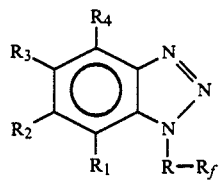 I or

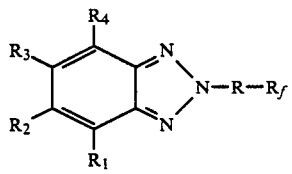 II wherein

R is an alkylene or alkenylene having 1 to 16 carbon atoms which is unsubstituted or substituted by hydroxyl or by lower alkoxy; and said alkylene is uninterrupted or is interrupted by a group selected from oxygen, sulfur, carboxamido, sulfonamido, aminocarbonyl, aminosulfonyl, carbonyloxy, sulfinyl and sulfonyl;

$R_f$ is a $C_4$–$C_{16}$-perfluoroalkyl or a $C_4$–$C_{16}$-perfluoroalkoxy; and $R_1$, $R_2$, $R_3$ and $R_4$ are each independently (a) hydrogen, halogen or hydroxyl; or (b) alkyl of up to 10 carbon atoms, lower alkoxy, lower alkanoyloxy or lower alkanoylamino each of which is independently unsubstituted or further substituted by $C_6$–$C_{10}$-aryl, $C_4$–$C_7$-cycloalkyl, $C_3$–$C_6$-azacycloalkyl, lower alkoxy, hydroxy, halogen, cyano or poly-lower alkyleneoxy; or $R_1$ and $R_4$ are hydrogen, $R_2$ is methoxy and $R_3$ is N-(1-ethyl-2-pyrrolidinylmethyl)carbamoyl.

2. A compound according to claim 1 wherein $R_1$, $R_2$, $R_3$ and $R_4$ are independently hydrogen, unsubstituted lower alkyl or unsubstituted lower alkoxy.

3. The compound of claim 1 wherein R is a $C_1$–$C_{12}$ alkylene which is unsubstituted or substituted as in claim 1.

4. The compound of claim 1 wherein R is a $C_2$–$C_{10}$ alkylene which is unsubstituted or substituted as in claim 1.

5. The compound of claim 1 wherein R is a $C_6$–$C_{10}$ alkylene which is unsubstituted or substituted as in claim 1.

6. The compound of claim 1 wherein said R is a $C_1$–$C_{16}$ alkylene interrupted by 1 or 2 oxygen atoms, or a group selected from sulfur, carboxamide and sulfonamide and is substituted by hydroxy.

7. The compound of claim 1 wherein said R is $C_1$–$C_{16}$ alkylene interrupted independently by one or two oxygen atoms or sulfur and is substituted by hydroxy.

8. The compound of claim 1 wherein said substituent on said R is hydroxy.

9. The compound of claim 1 wherein $R_f$ is $C_4$–$C_{16}$ perfluoroalkyl.

10. The compound of claim 1 wherein $R_f$ is $C_6$–$C_{12}$ perfluoroalkyl.

11. The compound of claim 1 wherein at least one of $R_1$–$R_4$ is hydrogen.

12. The compound of claim 1 wherein $R_1$–$R_4$ are each hydrogen.

* * * * *